United States Patent [19]

Halfman

[11] Patent Number: 4,816,419

[45] Date of Patent: * Mar. 28, 1989

[54] FLUORESCENCE LIGAND BINDING ASSAY USING CHARGE-MATCHED DYE AND SOLVENT COMPONENTS

[75] Inventor: Clarke J. Halfman, Highland Park, Ill.

[73] Assignee: University of Health Sciences/The Chicago Medical School, North Chicago, Ill.

[*] Notice: The portion of the term of this patent subsequent to Feb. 3, 2004 has been disclaimed.

[21] Appl. No.: 628,715

[22] Filed: Jul. 9, 1984

Related U.S. Application Data

[63] Continuation-in-part of Ser. No. 518,965, Aug. 1, 1983, Pat. No. 4,640,898.

[51] Int. Cl.$^4$ .......................................... G01N 33/533
[52] U.S. Cl. ................................. 436/546; 436/501; 436/536; 436/537; 436/800; 436/826; 436/829; 435/810
[58] Field of Search ............... 436/536, 537, 826, 829, 436/501, 546, 800; 435/810

[56] References Cited

U.S. PATENT DOCUMENTS

| | | | |
|---|---|---|---|
| 4,261,968 | 4/1981 | Ullman et al. | 436/537 |
| 4,452,903 | 6/1984 | Lee et al. | 436/826 |
| 4,454,232 | 6/1984 | Breglio et al. | 436/826 |
| 4,492,762 | 1/1985 | Wang et al. | 436/536 |

OTHER PUBLICATIONS

Jolley, et al., Fluorescence Polarization Immunoassay I. Monitoring Aminoglycoside Antibiotics in Serum and Plasma, *Clinical Chemistry*, vol. 27, No. 7, (1981), pp. 1190-1197.

Zuk, et al., Fluorescence Protection Immunoassay: A New Homogeneous Assay Technique, *Clinical Chemistry*, vol. 25, No. 9, (1979), pp. 1554-1560.

Smith, D. S., Enhancement of Fluoroimmunoassay of Thyroxine, *FEBS Letters*, vol. 77, No. 1, (1977), pp. 25-27.

Ullman, et al., Fluorescent Excitation Transfer Immunoassay, *J. Biol. Chem.*, vol. 251, No. 14, (1976), pp. 4172-4178.

Halfman, et al., Solvent Perturbation Fluorescence Immunoassay Technique, *Anal. Chem.*, vol. 57, (1985), pp. 1928-1930.

Shaw, et al., Estimation of Serum Gentamicin by Quenching Fluoroimmunoassay, *J. Clin. Path.*, vol. 30, (1977), pp. 526-531.

Halfman, et al., Optimization of Reactant Concentrations for Maximizing Sensitivities of Competitive Immunoassays, *Anal. Chem.*

O'Donnell, et al., Fluorescence Immunoassays, *Anal. Chem.*, vol. 51, (1979), pp. 33-40.

Love, et al., The Micelle-Analytical Chemistry Interface, *Anal. Chem.*, vol. 56, (1984), pp. 1132-1148.

Soini, et al., Fluorimmunoassay: Present Status and Key Problems, *Clinical Chemistry*, vol. 25, No. 3, (1979), pp. 353-361.

Burd, J. F., Fluoroimmunoassays in Drug Monitoring, *Clin. Chem. News*, Apr. 1982, p. 33.

Wong, et al., An Improved Response Variable for Fluorescence Polarization Immunoassays, *Clinical Chemistry*, vol. 28, No. 7, (1982), p. 1658.

(List continued on next page.)

*Primary Examiner*—Robert J. Warden
*Assistant Examiner*—Stephen C. Wieder
*Attorney, Agent, or Firm*—Norman Lettvin

[57] ABSTRACT

Fluorescence ligand binding assay of a sample containing an unknown amount of ligand is performed by making direct intensity measurements. In an immunoassay the sample is in a solution containing dye labeled analyte and an antibody specific to the analyte. Surfactant, added to the solution in an amount sufficient to form micelles, provides markedly different fluorescent intensity from bound and unbound labeled analyte if the surfactant ions and dye ions have the same charge polarity and the analyte moeity has the opposite charge polarity.

14 Claims, 2 Drawing Sheets

OTHER PUBLICATIONS

Halfman, et al., Method for Measuring the Binding of Small Molecules to Proteins from Binding-Induced Alterations of Physical-Chemical Properties, *Biochemistry*, vol. 11, No. 18, (1972), pp. 3493-3498.

Halfman, et al., Influence of pH and Electrolyte on the Fluorescence of Bovine Serum Albumin, *Biochim. Biophys. Acta*, vol. 243, (1971), pp. 284-293.

Halfman, et al., Nature of the Alteration of the Fluorescence Spectrum of Bovine Serum Albumin Produced by the Binding of Dodecyl Sulfate, *Biochim. Biophys. Acta*, vol. 243, (1971), pp. 294-303.

Tsuchiya, et al., Oscillatory Behavior in Fluorescence Intensity from Irradiated Sodium Dodecyl Sulfate Micellar Solutions of Zinc Porphyrin, *J. Am. Chem. Soc.*, vol. 103, (1981), pp. 7370-7371.

Corell, et al., Fluorescence Probes in Reversed Micelles., *J. Am. Chem. Soc.*, vol. 100, No. 4, (1978), pp. 1254-1262.

Lakowicz, et al., Binding of an Indole Derivative to Micelles as Quantified by Phase-Sensitive Detection of Fluorescence, *J. Biol. Chem.*, vol. 258, No. 9, (1983), pp. 5519-5524.

Guha, et al., Spectral and Fluorimetric Studies on the Effect of Surfactants on Thionine, *Proc. Indian Acad. Sci.*, vol. 91, No. 1, (1982), pp. 73-85.

Hirota, et al., Chem. Abstrs., vol. 99: 141526g, (1983).

Gratzel, et al., Modern Fluorescence Spectroscopy 2, New York, Plenum Press, (1976), p. 193.

Mukerjee, et al., Critical Micelle Concentrations . . ., U.S. Nat. Bureau. Stds., NSRDS-NBS 36, Washington, D.C., (1971), p. 52.

DeVenittis, et al., A Fluorometric Method for the Estimation . . ., *Anal. Biochem.*, vol. 115, (1981), pp. 278-286.

Law, K., Fluorescent Probe for Microenvironments:, *Photochemical Photobiology*, vol. 33, (1981), pp. 799-806

FLUORESCENCE LIGAND BINDING ASSAY USING CHARGE-MATCHED DYE AND SOLVENT COMPONENTS

This invention relates to an improved method and composition for fluorescence ligand binding assays, and, in particular, immunoassays. This is a continuation-in-part of co-pending application Ser. No. 518,965 filed Aug. 1, 1983, now U.S. Pat. No. 4,640,898 included herein by reference.

BACKGROUND OF THE INVENTION

A ligand binding assay is an analytical technique for measuring concentrations of substances that react selectively with specific binding proteins. Such substances are called ligands in the field of Biochemistry. Immunoassays to measure concentrations of antigens that react selectively with specific antibodies comprise a class of ligand binding assays.

Assay reagents in a ligand binding assay generally include:

1. A specific binding protein such as an antibody that specifically and strongly binds the substance to be measured, referred to as the analyte, the strong binding being characterized by an equilibrium dissociation constant less than about $10^{-8}M$; and
2. Labeled analyte.

The label provides a measurable property of the system for the purpose of monitoring the extent of binding of labeled analyte to antibody in a solution.

Fluorescent dyes have been shown to be useful as labels in homogeneous immunoassays as described in co-pending Application Ser. No. 518,965.

That application discloses a method and composition, using a nonprotein solute, for preferentially altering the relative intensities of bound and free dye labels. The method and composition make use of the present inventor's discovery that certain surfactants operate to effect differential fluorescence between bound and free labelled analyte. It would be desirable, however, to be able to characterize more precisely the surfactant-dye-analyte relationship that gives rise to differential fluorescence useful for ligand binding assays.

SUMMARY OF THE INVENTION

A feature of a preferred embodiment exemplifying the present invention is the use of micelles to sequester bound from free labeled analyte. The micelles are made using materials which bind the analyte moiety of labeled analyte, when the analyte is not bound to antibody, and do not bind the dye label moiety of the labeled analyte.

Micelles are aggregates of particles of colloidal dimensions formed by surfactants otherwise known as detergents, when dissolved above a critical concentration in water.

Fluorescent yield and degree of fluorescent polarization of certain dyes are very sensitive to the presence of micellar aggregates, as described in co-pending application Ser. No. 518,965.

It is therefore an object of the present invention to characterize more precisely, by reference to details of molecular structure, the relationships between dyes, analytes, and surfactants that lead to enhanced differential fluorescence between bound and free labeled analyte.

A method for fluorescence ligand binding assay exemplifying principles related to the present invention may be used to analyze a sample containing an unknown amount of the same analyte labeled with a suitable fluorescent dye. A measured amount of the sample together with a predetermined amount of the labeled analyte is placed in an aqueous solution to which is added a predetermined amount of antibody. A surfactant is also added to the solution in an amount greater than the threshold amount necessary to cause the surfactant to form micelles in the solution. Fluorescent emission from the solution is then measured. In an embodiment the surfactant preferentially quenches the emission from free labeled analyte to effect a homogeneous response. Measurement of the intensity of the fluorescence of the solution accordingly provides a measure of the fraction of labeled analyte which has been bound by the antibody in the solution.

The labeled analyte molecule comprises a dye moiety and an analyte moiety.

The dye moiety of a labeled analyte molecule in solution may have ionized groups within its structure. For example fluorescein dye, which may be used as a label, has two ionic groups which become negatively charged in water. Fluorescein, therefore, is effectively anionic, the effective charge polarity being negative. Rhodamine dye, on the other hand, acquires a positively charged structure at one location and a negatively charged structure at another location when placed in solution. A rhodamine moiety in solution is therefore an electric dipolar ion, or zwitterion.

Similarly, the analyte moiety of a labeled analyte molecule may ionize in solution either as an anion, a cation, a zwitterion, or may not ionize at all.

The micelle-forming surfactant molecules also ionize in solution. The surfactant ions may then bind to molecular moieties of opposite charge and repel moieties of the same charge. SDS ions in an aqueous solution are anions. Accordingly, SDS ions repel fluorescein ions. On the other hand, SDS will bind to the positive charge structure on the rhodamine moiety. Enhanced differential fluoresence emission occurs when the surfactant ions have the same charge as the dye ions and opposite charge from the analyte ions.

The charge effect is only one aspect of a more general phenomenon involving micelle binding to a moiety of a labeled analyte molecule. For example, hydrophobic analyte moieties are captured into the interior of micellar aggregates, as described by M. Gratzel, et al., "The Application of Fluorescence Techniques to the Study of Micellar System," in E. L. Wehry, Ed., *Modern Fluorescence Spectroscopy* 2, New York, Plenum Press (1976) p. 193.

Capture of labeled analyte molecules occurs preferentially for free labeled analyte. When the analyte is bound to antibody, capture is severely inhibited. Fluorescent emission and polarization is different from the labeled analyte molecules captures into micelle aggregates than from the molecules that are not captured.

An object of this invention, accordingly, is to provide an improved method for assaying the concentration of an analyte in a solution by measuring the intensity of fluorescence of labeled analyte in the solution.

Another object of this invention is to provide a composition including a surfactant characterized by its ionic charge for use in immunoassay to effect a preferential quenching of the free labeled analyte in a solution containing protein that binds specifically and strongly to the analyte.

These and other objects, advantages and features of the invention, as well as many of the particular advantages, become readily apparent from the following detailed description which is presented in conjunction with the accompanying drawings.

DETAILED DESCRIPTION OF A PREFERRED EMBODIMENT

A gentamicin immunoassay provides an example of a preferred embodiment according to principles derived from the present invention. The embodiment uses the surfactant sodium dodecyl sulphate (SDS) which is suitable for use with the dye fluorescein and the analyte gentamicin. A reactive derivative of fluorescein may be used to label gentamicin to make a fluorescein conjugate. Gentamicin antibody may also be prepared as described, for example in co-pending application Ser. No. 518,965 and references there cited.

Accordingly, a measured amount of a sample containing an unknown amount of gentamicin, a predetermined amount of conjugate, a predetermined amount of gentamicin antibody and sufficient SDS to form micelles is prepared in a buffered solution. Fluorescent emission from the solution may then be compared with the fluorescent emission from solutions that are similar except for the presence of known amounts of unlabeled gentamicin instead of the sample. The comparison of intensities thereby permits the amount of gentamicin in the sample to be determined.

Figure 1:
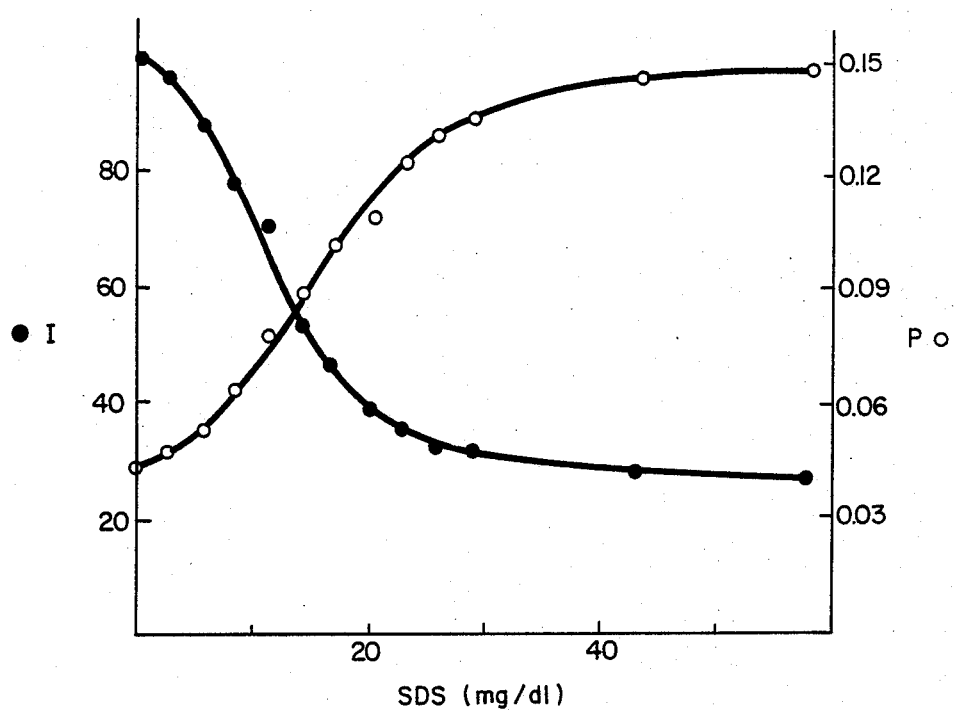
FIG. 1 illustrates the effect of sodium dodecyl sulphate (SDS) in solutions containing gentamicin labeled with fluorescein upon the intensity and polarization of the fluorescence.
Figure 2:
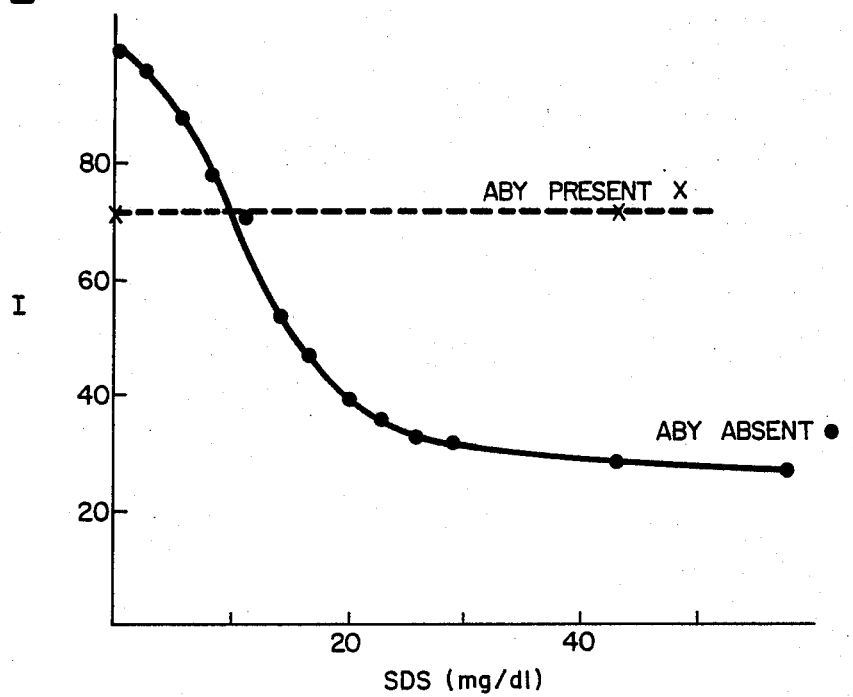
FIG. 2 illustrates the effect of SDS upon the fluroescent emission intensity of 10nM fluorescein labelled gentamicin in the presence and absence of excess gentamicin antibody.

As disclosed in co-pending application Ser. No. 518,965 and illustrated by FIG. 1, addition of SDS to free fluorescein labeled gentamicin in a 10 nM solution has a significant effect upon the intensity and polarization of fluorescence from the fluorescein dye component. The intensity is quenched, and the polarization increases, by about a factor of 4 as the SDS concentration is increased from 0–40 mg/dl. As illustrated in FIG. 2, however, the intensity of fluorescence from a 10 nM fluorescein labeled gentamicin solution containing excess gentamicin antibody (Aby) is substantially independent of SDS concentration.

Rhodamine B labeled thyroxin, on the other hand, does not exhibit a marked difference in fluorescence intensity between bound and free conjugates in the presence of SDS. As may be seen in FIG. 3, fluorescence from both bound and free rhodamine B labeled thyroxin conjugate in 10nM solution is enhanced by SDS as the SDS concentration is increased over the range 0–7 mg/dl.

The critical concentration for micelle formation is known to be in the range of about 20 mg/dl in electrolyte solutions, as shown in P. Mukerjee, et al., *Critical Micelle Concentrations in Aqueous Surfactants,* United States National Bureau of Standards NSRDS-NBS 36, Washington, D.C. (1971).

Anionic, cationic, and uncharged dyes in $\mu$M to mM solutions are known to interact with micelles regardless of the ionic nature of the detergent, as discussed by E. DeVenittis, et al., *A Fluorometric Method for the Estimation of the Critical Micelle Concentration of Surfactants,* Analytical Biochemistry 115 (1981) pp. 278–286 and K. Law, *Fluorescent Probe for Microenvironments: A New Probe for Michelle Solvent Parameters and Premicellar Aggregates,* Photochemical Photobiology 33 (1981) pp. 779–806. At concentrations in the $\mu$M to mM range there does not seem to be a preferential interaction between dye and micelle that is dependent upon the respectives charges of the reactants. However, a strong influence of charge on the dye-micelle interaction at dye concentrations in the nM range is suggested by the present investigation, as the ensuing discussion demonstrates.

Figure 4:
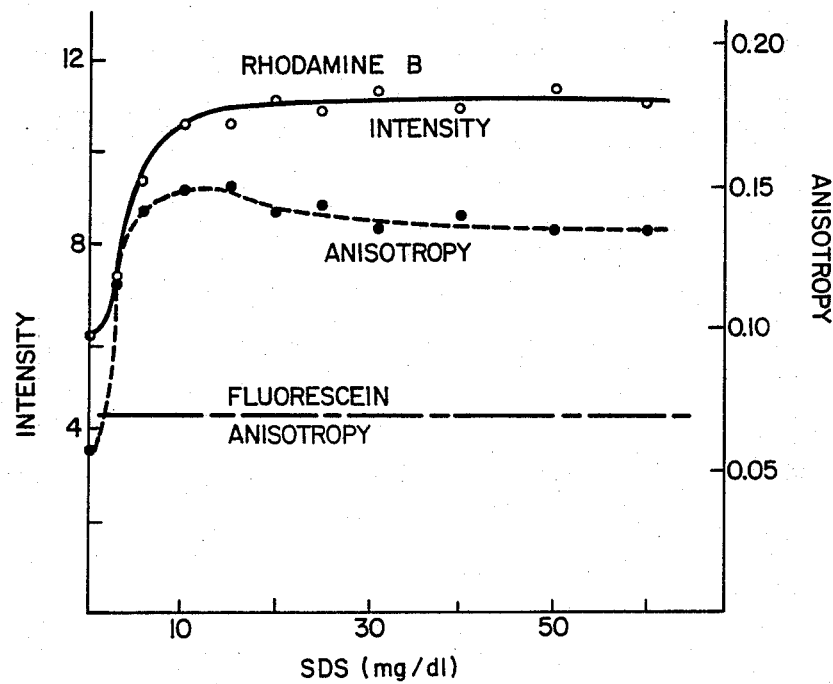
FIG. 4 illustrates the effect of SDS upon the emission intensity and anisotropy of 10nM rbodamine B and 10nM fluorescein.

The anisotropy (which is related to the polarization) of free fluorescein is not affected by SDS concentrations above the critical micelle concentration (40 mg/dl), as illustrated in FIG. 4. The emission intensity and polarization of free, but not bound, fluorescein labeled gentamicin conjugate is affected by SDS, as illustrated in FIG. 2. It may be concluded, therefore, that the gentamicin moiety of the conjugate interacts with the micellar aggregates.

Figure 3:
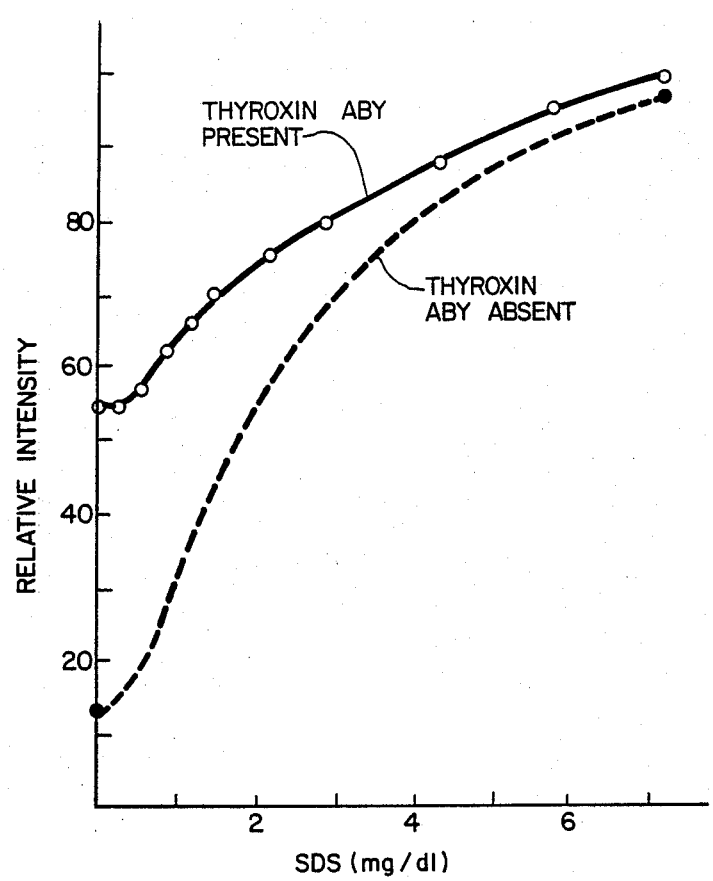
FIG. 3 illustrates the effect of SDS upon the emission intensity of 10nM rhodamine B labelled thyroxin in the presence and absence of excess thyroxin antibody.

Rhodamine B exhibits increased intensity and anisotropy (or polarization) in the presence of SDS, as illustrated in FIG. 4. Both free and bound Rhodamine B labeled thyroxin conjugate also exhibit increased intensity, as illustrated in FIG. 3. Fluorescein in solution is anionic, and Rhodamine B is zwitterionic. The SDS in solution is anionic. Thus, the SDS anions combine with the positive charge structure on the Rhodamine B zwitterionic moiety, whether the Rhodamine B is free in solution or is component of a bound or unbound conjugate. The SDS anions do not combine with fluorescein anions, whether those ions are free in solution as in FIG. 4, or combined in a conjugate bound to antibody as in FIG. 2. On the contrary, the SDS anions interact with the gentamicin cations of the fluorescein labeled gentamicin conjugate, but only if the gentamicin is unbound, as illustrated in FIGS. 1 and 2.

The differential effect of surfactant upon the fluorescence of bound and unbound dye labeled analyte is thus seen to be enhanced when the surfactant and the dye moiety ions have the same charge polarity and the analyte has the opposite charge polarity. That is, the enhancement occurs when both the surfactant and the dye are anions or both are cations in solution and the analyte moiety has, correspondingly, the opposite charge polarity.

Accordingly, a method for conducting a ligand binding assay to determine the concentration of an analyte in a sample containing an unknown amount of the analyte may comprise the steps of preparing an aqueous solution containing a measured amount of the sample, a predetermined amount of a conjugate including the analyte and a fluorescent dye, a predetermined amount of a protein that binds specifically and strongly to the analyte, and a surfactant, the surfactant concentration being greater than the micelle threshold, and measuring the intensity of fluorescent emission from the solution while irradiating the solution with electromagnetic radiation, the surfactant combining with the analyte moiety, while not combining with the dye moiety, of free conjugate and substantially not combining with conjugate bound to antibody to effect differential fluorescence between bound and unbound conjugate.

The fluorescence intensities, polarizations and anisotropies shown in FIGS. 1-4 were measured with a two-channel SLM model 4000 polarization spectrofluorometer. The spectrofluorometer was equipped with an excitation grating monochromator, excitation and emission Glann-Thompson polarizers, Hamamatsu R928 red-sensitive phototubes, and a water-jacketed cuvette compartment maintained at 30° C. with a Lauda RC-20T circulating water bath. Fluorescein emission was measured with an excitation wavelength of 492 nm (8nm band pass) and matched Turner 12 A2 filters (transmitting at wavelengths above 500 nm) in the emission beams. Rhodamine B emission was measured with an excitation wavelength of 545 nm and matched Turner 23A filters (transmitting at wavelengths above 570 nm) in the emission beams. Polarization values, denoted by "P" in the FIGS., were determined from measurements with vertically polarized excitation and with the emission polarizers located at right angles to both the excitation beam direction and the excitation beam polarization plane.

The polarization was obtained by measuring the emission with the emission polarizers oriented in the vertical direction, denoted by V, and the horizontal direction, denoted by H. The polarization was then calculated from the formula.

$$P = (V-H)/(V+H) \qquad (1)$$

The anisotropy A was calculated from the formula $$A = (V-H)/(V+2H) \qquad (2)$$

where the quantity $V+2H$ is proportional to the total number of emitters excited by the excitation beam.

It will of course, be understood that modification of the present invention in its various aspects will be apparent to those skilled in the art, some being apparent only after study and others being a matter of routine design. For example, ligands other than gentamicin, dyes other than fluorescein and solutes other than SDS may be used in connection with the present invention. Ligands, dyes and solutes may be chosen to exploit forces other than the electrostatic forces described herein for effecting capture of analyte moieties by solute. For example, analyte moieties that do not ionize in solution, but may be bound within micellar structure by hydrophobic forces, would do just as well. As such, the scope of the invention should not be limited by the particular method and combination herein described but should be defined only by the appended claims and equivalents thereof.

What is claimed is:

1. A method for conducting a ligand binding assay, to determine the concentration of an analyte in a sample containing an unknown amount of the analyte, comprising the steps of:

preparing an aqueous solution containing a measured amount of the sample, a predetermined amount of a conjugate including a moiety of the analyte and a moiety of a fluorescent dye, fluorescein, a predetermined amount of a protein that binds specifically to the analyte, and a surfactant, sodium dodecyl sulfate, the surfactant concentration being greater than the surfactant's micelle threshold, so as to form surfactant micelles in the solution;

the binding of portein to analyte in the solution being strong, and being so characterized by reason of an equilibrium dissociation constant less than about $10^{-8}M$;

measuring the intensity of fluorescent emission from said solution while irradiating said solution with electromagnetic radiation; and said micelles of surfactant combining with the analyte moiety, but not combining with the dye moiety of free conjugate, and thereby substantially not combining with conjugate bound to said protein, so as to effect differential fluorescence between bound conjugate and free conjugate.

2. A method for conducting a ligand binding assay in accordance with claim 1 wherein said dye moiety and said surfactant ions in solution have the same charge polarity which is opposite to the charge polarity of said analyte moiety unbound to said protein.

3. A composition for effecting contrast between fluorescent emission from bound and free analyte in a solution containing protein that specifically binds to the analyte, comprising:

the protein being one that binds strongly to the analyte by reason of having an equilibrium dissociation constant less than about $10^{-8}M$;

a selected amount of fluorescent dye combined with the analyte solution to form a conjugate having both a dye moiety and an analyte moiety;

a surfactant in the solution at a concentration greater than the surfactant's critical micelle concentration, so as to form surfactant micelles; and said surfactant micelles being operative with said conjugate in the solution to combine preferentially with said analyte moiety, when said analyte moiety is unbound to the protein, so as to affect differentially the fluorescent emission from said conjugate, when said conjugate is respectively bound and free and when the solution is irradiated with electromagnetic radiation.

4. A composition according to claim 3 wherein said conjugate and said solute ionize in solution, said dye moiety and said solute ion having the same charge polarity and said analyte ion, when unbound to protein, having the opposite charge polarity.

5. A composition in accordance with claim 3 in which said fluorescent dye is fluorescein.

6. A composition in accordance with claim 3 in which said solute is sodium dodecyl sulphate.

7. A composition in accordance with claim 6 in which said fluorescent dye is fluorescein.

8. A kit of reagents, for providing differential fluorescent emission from respectively bound and free labeled analyte contained in an aqueous solution when the solution is irradiated with electromagnetic radiation; said kit comprising:

a predetermined amount of a protein that is to be added to the aqueous solution and which will bind specifically and strongly to the analyte, by reason of having an equilibrium dissociation constant that is less than about $10^{-8}M$;

a fluorescent dye that is to be combined with the analyte to form a conjugate of labeled analyte;

the charge polarity of the fluorescent dye being opposite to the charge polarity of the analyte moiety;

a surfactant for addition to the aqueous solution in an amount sufficient to form surfactant micelles in the solution; and the surfactant ions having charge polarity opposite to the charge polarity of the analyte component of said conjugate when said analyte component is free, and the same charge polarity as the dye component of said conjugate, and being cooperative with said conjugate, when irradiated with electromagnetic radiation, to effect differential fluorescence between conjugate having respective bound and free analyte components.

9. A combination in accordance with claim 8 in which said fluorescent dye is fluorescein.

10. A combination in accordance with claim 9 in which said fluorescein is combined with the analyte as fluorescein isothiocyanate.

11. A combination in accordance with claim 10 in which said surfactant is sodium dodecyl sulphate.

12. A combination in accordance with claim 9 in which said surfactant is sodium dodecyl sulfate.

13. A combination in accordance with claim 8 in which said surfactant is sodium dodecyl sulfate.

14. A kit of reagents for use in effecting differential fluorescent emission from respectively bound and unbound labeled analyte contained in a solution, the solution containing specific binding protein to bind strongly to the analyte by reason of said protein having an equilibrium dissociation constant that is less than about $10^{-8}M$;

the kit including: a fluorescent dye that is to be combined with analyte to form a conjugate; and detergent micelles for introduction into the solution and which when dissolved in the solution provides ions of opposite charge polarity from the analyte component of siad conjugate, and which causes said conjugate to fluoresce differentially when analyte portions are respectively bound and when unbound.

* * * * *